United States Patent
Qu et al.

(10) Patent No.: US 11,702,639 B2
(45) Date of Patent: Jul. 18, 2023

(54) COLUMN-BASED FULLY SCALABLE RAAV MANUFACTURING PROCESS

(71) Applicant: SPARK THERAPEUTICS, INC., Philadelphia, PA (US)

(72) Inventors: Guang Qu, Sicklerville, NJ (US); Younghoon Oh, Bryn Mawr, PA (US); Lin Lu, Wayne, PA (US); John Fraser Wright, Princeton, NJ (US)

(73) Assignee: SPARK THERAPEUTICS, INC., Philadelphia, PA (US)

( * ) Notice: Subject to any disclaimer, the term of this patent is extended or adjusted under 35 U.S.C. 154(b) by 1251 days.

(21) Appl. No.: 16/088,743

(22) PCT Filed: Mar. 31, 2017

(86) PCT No.: PCT/US2017/025396
§ 371 (c)(1),
(2) Date: Sep. 26, 2018

(87) PCT Pub. No.: WO2017/173283
PCT Pub. Date: Oct. 5, 2017

(65) Prior Publication Data
US 2020/0299650 A1    Sep. 24, 2020

Related U.S. Application Data (60) Provisional application No. 62/316,252, filed on Mar. 31, 2016.

(51) Int. Cl.
| | |
|---|---|
| C12N 7/00 | (2006.01) |
| B01D 15/34 | (2006.01) |
| B01D 15/36 | (2006.01) |
| B01D 61/14 | (2006.01) |
| B01D 15/38 | (2006.01) |
| C12N 1/06 | (2006.01) |

(52) U.S. Cl.
CPC ............... *C12N 7/00* (2013.01); *B01D 15/34* (2013.01); *B01D 15/362* (2013.01); *B01D 15/363* (2013.01); *B01D 15/3804* (2013.01); *B01D 61/145* (2013.01); *C12N 1/06* (2013.01); *B01D 2315/16* (2013.01); *C12N 2750/14142* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 5,981,716 A * | 11/1999 | Zanette | C07K 14/505 530/416 |
| 6,593,123 B1 | 7/2003 | Wright et al. | |
| 7,419,817 B2 | 9/2008 | Chiorini et al. | |
| 11,261,463 B2 * | 3/2022 | Qu | C12N 15/86 |
| 2013/0072548 A1 | 3/2013 | Wright et al. | |
| 2014/0248695 A1 | 9/2014 | Bovolenta et al. | |
| 2015/0024467 A1 | 1/2015 | Sheldon et al. | |

FOREIGN PATENT DOCUMENTS

| | | | |
|---|---|---|---|
| CN | 102803478 A | 11/2012 | |
| CN | 102947453 A | 2/2013 | |
| EP | 2325194 A1 * | 5/2011 | C07K 1/36 |
| JP | 2012-529917 A | 11/2012 | |
| JP | 2013-517798 A | 5/2013 | |
| WO | 2004/113494 A2 | 12/2004 | |
| WO | 2010/148143 A1 | 12/2010 | |
| WO | 2011/094198 A1 | 8/2011 | |

OTHER PUBLICATIONS

Wadsworth et al. Scaleable chromatographic purification process for recombinant adeno-associated virus (rAAV), J. Gene Medicine, 2000, 2, 444-456 (Year: 2000).*
Kotin et al. "Serum-free production and column purification of adeno-associated virus type 5" J Virological Methods 114 (2003) 115-124 (Year: 2003).*
Samulski et al. "Viral receptors and vector purification: new approaches for generating clinical-grade reagents" Nature Medicine, vol. 5, May 1999, pp. 587-588 (Year: 1999).*
GE Healthcare "Ion Exchange Chromatography: principles and methods" 2016. (Year: 2016).*
Qu et al. "PEG-modulated column chromatography for purification of recombinant adeno-associated virus serotype 9" J. Virological Methods, 173 (2011) pp. 99-107 (Year: 2011).*
Blouin, V., et al., Improving rAAV production and purification: towards the definition of a scaleable process, The Journal of Gene Medicine, Feb. 10, 2004, 6(S1):S223-S228, Abstract.
Qu, W., et al., Separation of adeno-associated virus type 2 empty particles from genome containing vectors by anion-exchange column chromatography, Journal of Virological Methods, 140(1-2):183-192 (2007).
Qu, W., et al., Scalable Downstream Strategies for Purification of Recombinant Adena-Associated Virus Vectors in Light of the Properties,Current Pharmaceutical Biotechnology, vol. 16, Jan. 1, 2015 (Jan. 1, 2015), pp. 684-695.

(Continued)

Primary Examiner — Daniel E Kolker
Assistant Examiner — James L Rogers
(74) Attorney, Agent, or Firm — Pillsbury Winthrop Shaw Pittman LLP; Robert M. Bedgood (57) ABSTRACT

In accordance with the invention, provided herein are methods for purifying recombinant adeno-associated (rAAV) vector particles.

47 Claims, 3 Drawing Sheets

(56) References Cited

OTHER PUBLICATIONS

Zhou, J., et al., PEG-modulated column chromatography for purification of recombinant adeno-associated virus serotype 9, Journal of Virological Methods, 173(1):99-107 (2011).
Vijayaragavan K. S., Virus purification, detection and removal. Dissertation, Michigan Technological University, 2014, pp. 1-270.
Clement et al., "Manufacturing of recombinant adeno-associated viral vectors for clinical trials", Molecular Therapy—Methods & Clinical Development, Mar. 16, 2016, pp. 1-7, vol. 3: 16002.

* cited by examiner

FIG. 1

All column purification process

FIG. 2

All column purification process

- Ion Exchange column chromatography
- Size Exclusion column chromatography
- Affinity column chromatography
- PEG-modulated column chromatography
- Surfactant-enhanced column chromatography

FIG. 3

All column purification process

1. AVB
2. AVB > CIEX > AIEX
3. AVB > AIEX
4. CIEX > UF/DF > SEC > AIEX (50-60

50-60% vector recovery

COLUMN-BASED FULLY SCALABLE RAAV MANUFACTURING PROCESS

RELATED APPLICATIONS

This patent application is the National Phase of International Application No. PCT/US2017/025396, filed Mar. 31, 2017, which designated the U.S. and that International Application was published under PCT Article 21(2) in English, which claims the benefit of priority to U.S. Provisional Patent Application No. 62/316,252, filed Mar. 31, 2016. The entire contents of the foregoing applications are incorporated herein by reference, including all text, tables, sequence listing and drawings.

INTRODUCTION

Gene delivery is a promising method for the treatment of acquired and inherited diseases. A number of viral-based systems for gene transfer purposes have been described, including adeno-associated virus (AAV)-based systems.

AAV is a helper-dependent DNA parvovirus that belongs to the genus *Dependovirus*. AAV requires helper virus function, e.g., adenovirus, herpes virus, or vaccinia, in order for a productive infection to occur. In the absence of a helper virus functions, AAV establishes a latent state by inserting its genome into a host cell chromosome. Subsequent infection by a helper virus rescues the integrated viral genome, which can then replicate to produce infectious AAV progeny.

AAV has a wide host range and is able to replicate in cells from any species in the presence of a suitable helper virus. For example, human AAV will replicate in canine cells co-infected with a canine adenovirus. AAV has not been associated with any human or animal disease and does not appear to adversely affect the biological properties of the host cell upon integration.

AAV vectors can be engineered to carry a heterologous nucleic acid sequence of interest (e.g., a selected gene encoding a therapeutic protein, an inhibitory nucleic acid such as an antisense molecule, a ribozyme, a miRNA, etc.) by deleting, in whole or in part, the internal portion of the AAV genome and inserting the nucleic acid sequence of interest between the ITRs. The ITRs remain functional in such vectors allowing replication and packaging of the rAAV containing the heterologous nucleic acid sequence of interest. The heterologous nucleic acid sequence is also typically linked to a promoter sequence capable of driving expression of the nucleic acid in the patient's target cells. Termination signals, such as polyadenylation sites, can also be included in the vector.

The construction of infectious recombinant AAV (rAAV) vectors has been described in a number of publications. See, e.g., U.S. Pat. Nos. 5,173,414 and 5,139,941; International Publication Numbers WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; and Kotin, R. M. (1994) Human Gene Therapy 5:793-801.

Recombinant adeno-associated virus (AAV) vectors have shown excellent therapeutic promise in several early phase clinical trials by multiple groups. Development of this new class of biologic product towards approval will involve improvements in vector characterization and quality control methods, including a better understanding of how vector design and manufacturing process parameters affect impurity profiles in clinical grade vectors.

An important objective in the design of rAAV production and purification systems is to implement strategies to minimize/control the generation of production related impurities such as proteins, nucleic acids, and vector-related impurities, including wild-type/pseudo wild-type AAV species (wtAAV) and AAV-encapsidated residual DNA impurities. Removal of impurities in AAV vectors is complicated due to the way rAAV vectors are produced. In one production process, rAAV vectors are produced by a transient transfection process using three plasmids. Significant amounts of plasmid DNA are introduced into the cells to produce rAAV vectors. In addition, when rAAV vectors are released from the producing cells, cellular proteins and nucleic acids are co-released. Considering that the rAAV vector represents only about 1% of the biomass, it is very challenging to purify rAAV vectors to a level of purity which can be used as a clinical human gene therapy product. (Smith P H Wright J F. Qu G. et al 2003, *Mo. Therapy*, 7:8348; Chadeuf G. et al, *Mo. Therapy* 2005, 12:744. Report from the CHMP gene therapy expert group meeting. European Medicines Agency EMEA/CHMP 2005, 183989/2004).

Development of manufacturing processes to purify recombinant AAV as a product to treat human disease should achieve the following objectives: 1) consistent vector purity, potency and safety; 2) manufacturing process scalability; and 3) acceptable cost of manufacturing. Current 'industry standard' scalable AAV vector purification processes do not adequately achieve removal of impurities, which is important to meet the first objective listed above (consistent vector purity, potency and safety). Moreover, failure to adequately remove impurities using current industry-standard scalable purification processes has occurred because: 1) development of purification processes of viral products such as recombinant AAV for applications other than vaccines (in which an immune response is typically sought rather than avoided) is relatively new; 2) many groups involved in the development of scalable purification processes for AAV vectors have been unaware of the high levels of vector-related impurities and/or have assumed that such impurities will not contribute to a clinically significant vector immunogenicity; and 3) it is technically challenging to develop scalable purification processes suitable for the industry scale manufacture of rAAV vectors.

SUMMARY

In accordance with the invention, provided herein, in some aspects, is a method for purifying recombinant adeno-associated (rAAV) vector particles, where the method comprises the steps of, (a) harvesting cells and/or cell culture supernatant comprising rAAV vector particles to produce a harvest; (b) optionally concentrating the harvest produced in step (a) to produce a concentrated harvest; (c) lysing the harvest produced in step (a) or the concentrated harvest produced in step (b) to produce a lysate; (d) treating the lysate to reduce contaminating nucleic acid in the lysate thereby producing a nucleic acid reduced lysate; (e) filtering the nucleic acid reduced lysate produced in step (d) to produce a clarified lysate, and optionally diluting the clarified lysate to produce a diluted clarified lysate; (f) subjecting the clarified lysate or diluted clarified lysate produced in step (e) to anion or cation exchange column chromatography to produce a column eluate comprised of rAAV vector particles, and optionally concentrating the column eluate to produce a concentrated column eluate; (g) subjecting the column eluate or the concentrated column eluate produced in step (f) to size exclusion column chromatography to produce a second column eluate comprised of rAAV vector particles, thereby separating rAAV vector particles from protein impurities, and optionally diluting the second column eluate to produce a diluted second column eluate; (h) subjecting the second column eluate or the diluted second column eluate produced in step (g) to cation or anion exchange column chromatography to produce a third column eluate comprised of rAAV vector particles thereby separating rAAV vector particles from protein or other production impurities, and optionally concentrating the third column eluate to produce a concentrated third column eluate; and (i) filtering the third column eluate or the concentrated third column eluate produced in step (h) thereby producing purified rAAV vector particles. The following embodiments and aspects refer to one or more of steps (a) through (h) above.

In certain embodiments step (f) comprises subjecting the clarified lysate or diluted clarified lysate produced in step (e) to anion exchange chromatography, and/or step (h) comprises subjecting the second column eluate or the diluted second column eluate produced in step (g) to cation exchange column chromatography. In certain embodiments step (f) comprises subjecting the clarified lysate or diluted clarified lysate produced in step (e) to cation exchange chromatography, and/or step (h) comprises subjecting the second column eluate or the diluted second column eluate produced in step (g) to anion exchange column chromatography.

In some aspects the concentrating of step (b) and/or step (f) and/or step (h) is by ultrafiltration/diafiltration, optionally by tangential flow filtration. In some embodiments the concentrating of step (b) reduces the volume of the harvested cells and cell culture supernatant by about 2-10 fold. In certain embodiments, the concentrating of step (f) reduces the volume of the column eluate by about 5-20 fold. In some aspects the lysing of the harvest produced in step (a) or the concentrated harvest produced in step (b) is by microfluidization In certain embodiments, after step (b) and before step (c), the method comprises a step (b)(i). In certain embodiments step (b)(i) comprises reducing contaminating nucleic acid in the lysate. In some embodiments step (b)(i) comprises treating the lysate with a nuclease thereby reducing contaminating nucleic acid. In certain embodiments the nuclease comprises benzonase.

In some embodiments, filtering the clarified lysate or the diluted clarified lysate of step (e) is via a filter having a pore diameter of between about 0.1 and 0.8 microns, inclusive. In certain embodiments, the diluting of the clarified lysate or the diluted clarified lysate of step (e) is with an aqueous buffered acetate solution.

In some embodiments, the diluting of the second column eluate of step (g) is with an aqueous buffered acetate solution. In certain embodiments the aqueous buffered acetate solution has a pH of between about 4.0 and 7.0, inclusive.

In some embodiments the rAAV vector particles are formulated with a surfactant to produce an AAV vector formulation. In certain embodiments, the rAAV vector particles resulting from step (i) are formulated with a surfactant to produce an AAV vector formulation.

In some embodiments the cation or anion exchange column chromatography of step (f) comprises polyethylene glycol (PEG) modulated column chromatography. In certain embodiments the cation or anion exchange column chromatography of step (f) comprises washing the column with a PEG solution prior to elution of the rAAV vector particles from the column. In certain embodiments the PEG in the PEG solution has an average molecular weight in a range of about 1,000 to 50,000, inclusive. In some embodiments the cation or anion exchange column of step (e) comprises washing the column with an aqueous surfactant solution prior to elution of the rAAV vector particles from the column. In certain embodiments the cation or anion exchange column of step (h) comprises washing the column with a surfactant solution prior to elution of the rAAV vector particles from the column. In some embodiments a PEG solution and/or the surfactant solution comprises an aqueous Tris-Cl/NaCl buffer or an aqueous phosphate/NaCl buffer. In certain embodiments the NaCl buffer comprises between about 20-250 mM NaCl, inclusive, or between about 50-200 mM NaCl, inclusive.

In some embodiments the rAAV vector particles are eluted from the cation or anion exchange column of step (f) in an aqueous Tris-Cl/NaCl buffer. In certain embodiments the Tris-Cl/NaCl buffer comprises 50-200 mM NaCl. In certain embodiments the rAAV vector particles are eluted from the cation or anion exchange column of step (h) in an aqueous phosphate/NaCl buffer. In some embodiments the phosphate/NaCl buffer comprises between about 100-500 mM NaCl, inclusive. In certain embodiments the cation exchange column of step (f) comprises a quaternary ammonium functional group. In certain embodiments, the quaternary ammonium functional group comprises a quaternized polyethyleneimine.

In certain embodiments, the size exclusion column, e.g., of step (g) has a separation rage (Molecular weight) between about 10,000 and 600,000, inclusive. In some embodiments the cation exchange column of step (h) comprises a sulfonic acid. In some embodiments the cation exchange column of step (h) comprises sulphopropyl.

In certain embodiments, the methods disclosed herein exclude a step of cesium chloride gradient ultracentrifugation.

In certain embodiments the rAAV vector particles comprise a transgene that encodes a nucleic acid selected from the group consisting of a siRNA, an antisense molecule, miRNA a ribozyme and a shRNA. In some embodiments the rAAV vector particles comprise a transgene that encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

In some embodiments the rAAV vector particles comprise a transgene that encodes a gene product selected from the group consisting of thrombopoietin (TPO), interleukins (IL1 through IL-17), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, class I and class II MHC molecules.

In certain embodiments the rAAV vector particles comprise a transgene encoding a protein useful for correction of in born errors of metabolism selected from the group consisting of carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, RPE65, H-protein, T-protein, a cystic fibrosis transmembrane regulator (CFTR) sequence, and a dystrophin cDNA sequence. In some embodiments the rAAV vector particles comprise a transgene that encodes Factor VIII or Factor IX.

In certain embodiments a method described herein recovers approximately 40-70% of the total rAAV vector particles from the harvest produced in step (a) or the concentrated harvest produced in step (b). In some embodiments a method described herein produces rAAV vector particles having a greater purity than rAAV vector particles produced or purified by AAV affinity column purification. In some embodiments a method described herein produces rAAV vector particles having a greater purity than rAAV vector particles produced or purified by an AAV affinity column combined with an anion exchange column purification. In certain embodiments a method described herein produces rAAV vector particles having a greater purity than rAAV vector particles produced or purified by an AAV affinity column combined with an anion exchange column and a cation exchange purification.

In certain aspects, rAAV vector particles (e.g., bona fide rAAV vector particles) are derived from an AAV selected from the group consisting of AAV1, AAV2, AAV3, AAV4, AAV5, AAV6, AAV7, AAV8, AAV9 and AAV10, AAV tyr$^{-3}$, (3YAF, see, e.g., U.S. Pat. No. 8,445,267) AAVcapsid with peptide modifications, such as a cell targeting peptide.

In some aspects the bona fide rAAV vector particles are present in the last (e.g., third column eluate of step (h) at a concentration of about 100 mg/mL. In some aspects bona fide rAAV vector particles are present in the last (e.g., third column eluate of step (h) at a concentration of $10^{15}$ particles per mL, or more, $10^{16}$ particles per mL, or more, or, e.g., $10^{17}$ particles per mL, or more.

DETAILED DESCRIPTION

Figure 1:
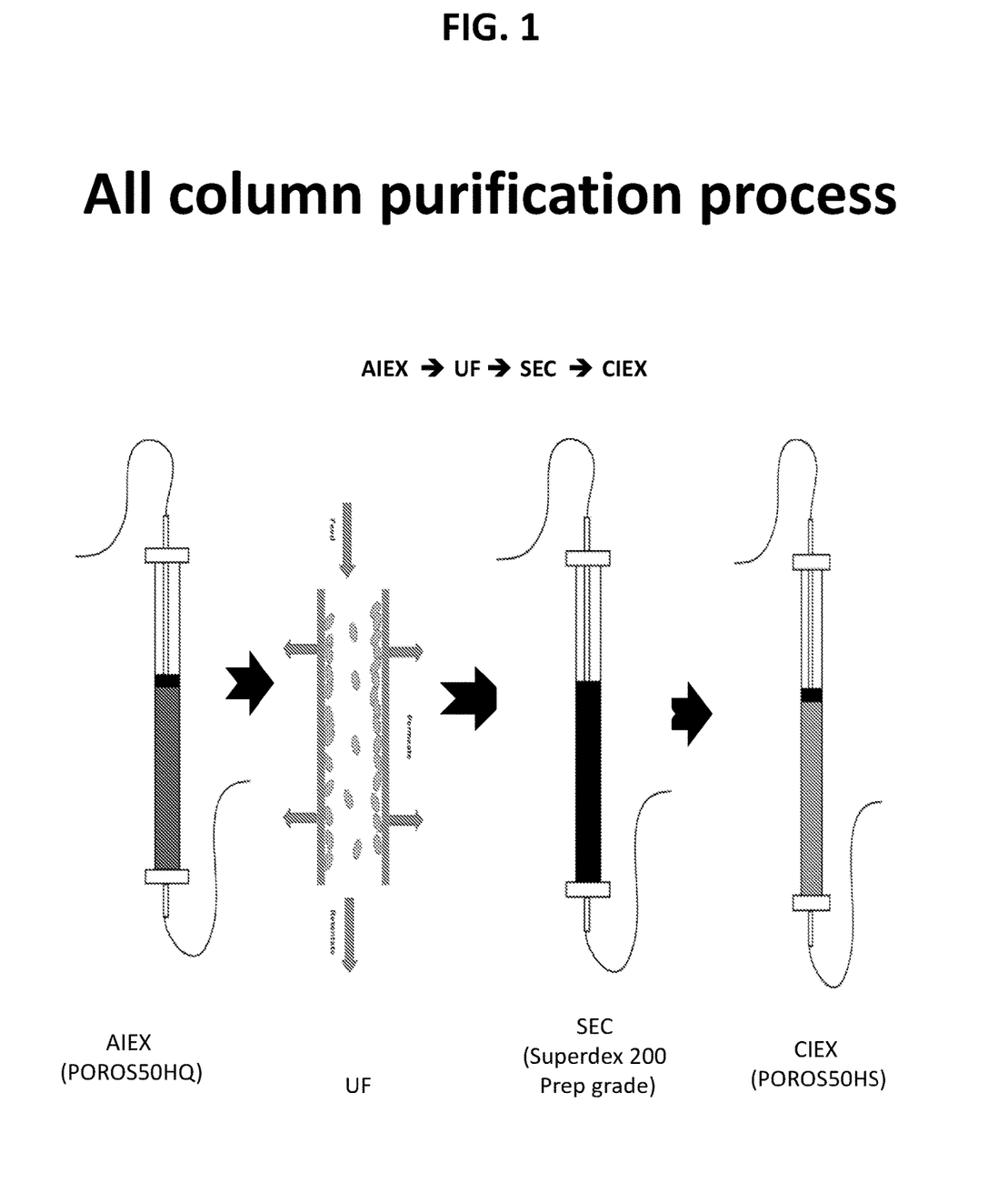
FIG. 1 shows a representative all column AAV purification scheme with anion, gel filtration (size exclusion) and cation chromatography columns. AIEX—anion exchange chromatography; UF/DF—ultrafiltration/Diafiltration; SEC—size exclusion chromatography; and CIEX, cation exchange chromatography. The scheme can also be performed in reverse order.
Figure 2:
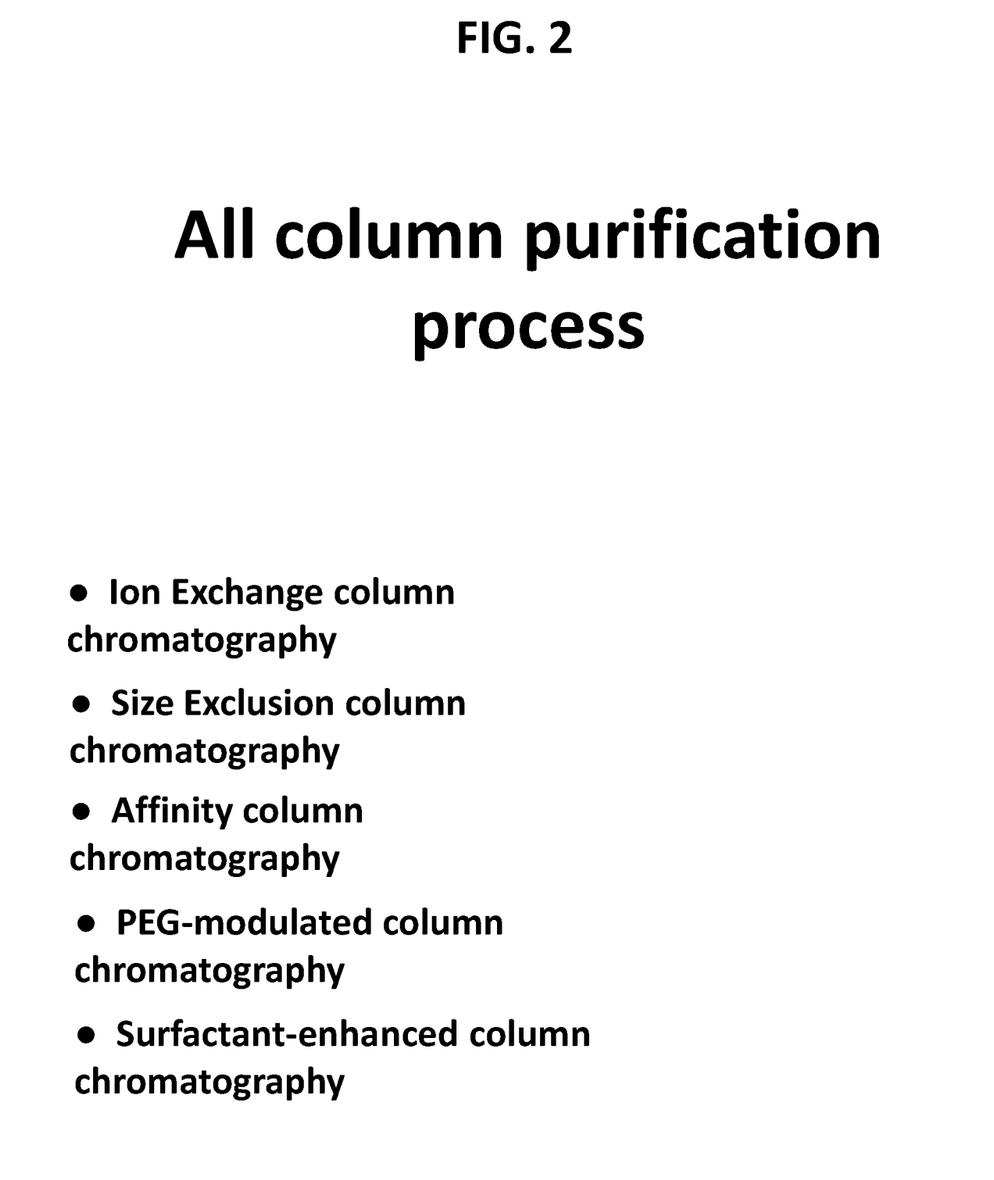
FIG. 2 shows various design options for developing a column-based AAV purification process.
Figure 3:
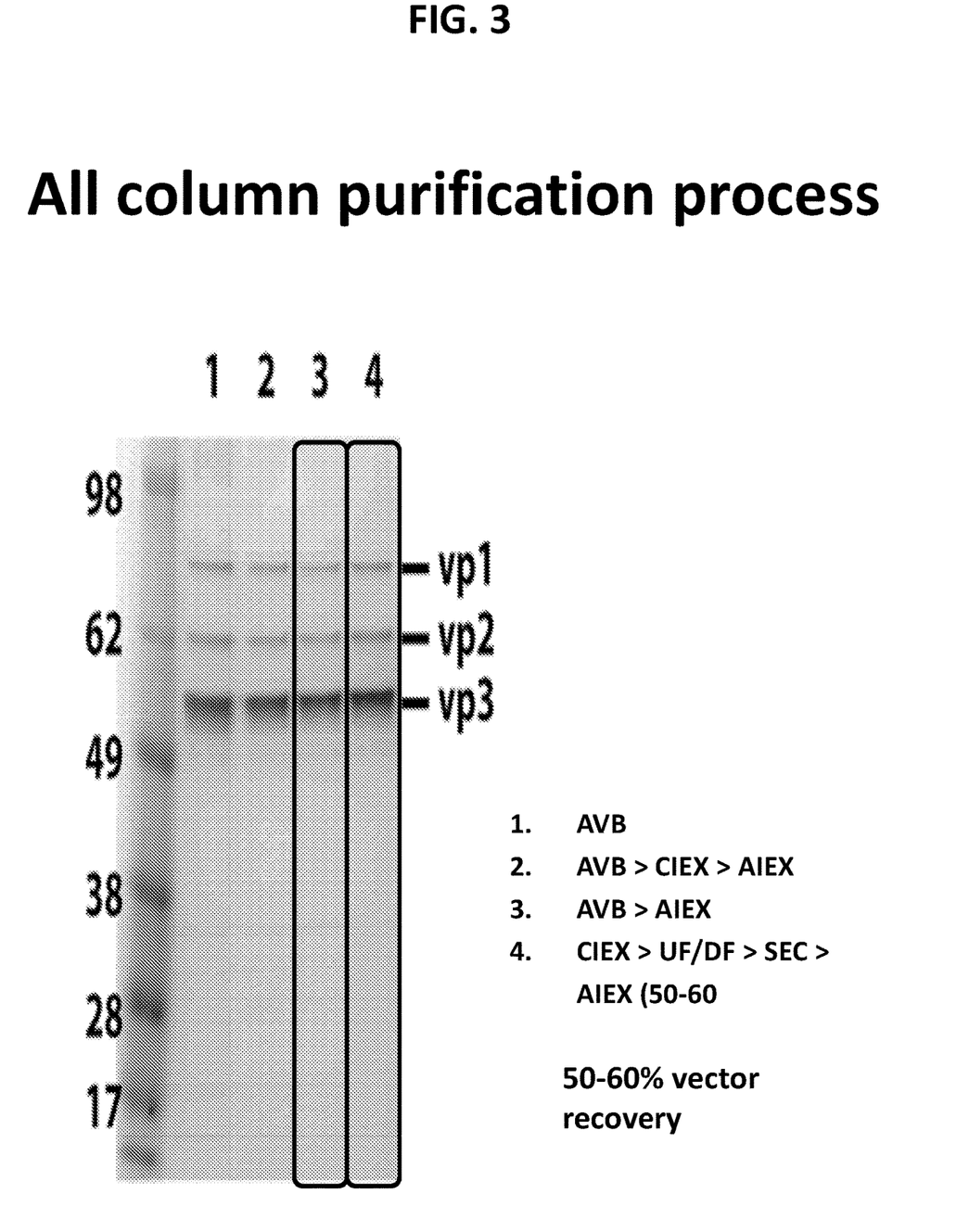
FIG. 3 shows comparative results of AAV purification with four (1-4) different purification schemes: (1) AVB (antibody-based AAV affinity column); and combinations of different columns, namely (2) AVB (AAV affinity column) in combination with AIEX and CIEX; (3) AVB (AAV affinity column) in combination with AIEX; and (4) AIEX in combination with SEC—size exclusion and CIEX chromatography. The results show that impurities are less in the purification scheme (4) than schemes (1) and (2), and also likely less than scheme (3). UF/DF—ultrafiltration/diafiltration was used to concentrate as shown, but is optionally included in the column AAV purification scheme.

The invention provides a recombinant adeno-associated virus (AAV) vector (rAAV) vector purification platform that includes unique features that distinguish it from current 'industry-standard' scalable AAV vector purification processes: 1) a modular platform process that can be used for purification of different AAV vector serotypes/capsid variants, including removal of in process impurities and in production related impurities. 2) a unique combination of chromatography steps and process steps that confers unexpected scalability to purify many different serotypes/pseudotypes of rAAV vectors.

Impurities include AAV vector production related impurities which include proteins, nucleic acids (e.g., DNA), cellular components such as intracellular and membrane components which are impurities distinct from the AAV vectors. The term "vector-production related impurities" refers to any components released during the AAV production process.

Bona fide AAV vectors refer to AAV vector particles comprising the heterologous nucleic acid (e.g., transgene) which are capable of infecting target cells. The phrase excludes empty AAV capsids, AAV vectors lacking full inserts in the packaged genome or AAV vectors containing contaminating host cell nucleic acids. In certain embodiments, bona fide AAV vectors refer to AAV vector particles that also lack contaminating plasmid sequences in the packaged vector genome.

"Empty capsids" and "empty particles" refer to an AAV particle or virion that includes an AAV capsid shell but that lacks in whole or part the genome comprising the heterologous nucleic acid sequence flanked on one or both sides by AAV ITRs. Such empty capsids do not function to transfer the heterologous nucleic acid sequence into the host cell or cells within an organism.

The term "vector" refers to small carrier nucleic acid molecule, a plasmid, virus (e.g., AAV vector), or other vehicle that can be manipulated by insertion or incorporation of a nucleic acid. Vectors can be used for genetic manipulation (i.e., "cloning vectors"), to introduce/transfer polynucleotides into cells, and to transcribe or translate the inserted polynucleotide in cells. An "expression vector" is a vector that contains a gene or nucleic acid sequence with the necessary regulatory regions needed for expression in a host cell. A vector nucleic acid sequence generally contains at least an origin of replication for propagation in a cell and optionally additional elements, such as a heterologous nucleic acid sequence, expression control element (e.g., a promoter, enhancer), intron, inverted terminal repeats (ITRs), optional selectable marker, polyadenylation signal.

An AAV vector is derived from adeno-associated virus. AAV vectors are useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous nucleic acid sequences (e.g., therapeutic proteins and agents) to human patients without causing substantial AAV pathogenesis or disease.

The term "recombinant," as a modifier of vector, such as rAAV vectors, as well as a modifier of sequences such as recombinant polynucleotides and polypeptides, means that the compositions have been manipulated (i.e., engineered) in a fashion that generally does not occur in nature. A particular example of a recombinant AAV vector would be where a nucleic acid that is not normally present in the wild-type AAV genome is inserted within the viral genome. An example of would be where a nucleic acid (e.g., gene) encoding a therapeutic protein or polynucleotide sequence is cloned into a vector, with or without 5', 3' and/or intron regions that the gene is normally associated within the AAV genome. Although the term "recombinant" is not always used herein in reference to AAV vectors, as well as sequences such as polynucleotides, recombinant forms including AAV vectors, polynucleotides, etc., are expressly included in spite of any such omission.

A "rAAV vector" is derived from the wild type genome of a virus, such as AAV by using molecular methods to remove the wild type genome from AAV genome, and replacing with a non-native (heterologous) nucleic acid, such as a nucleic acid encoding a therapeutic protein or polynucleotide sequence. Typically, for AAV one or both inverted terminal repeat (ITR) sequences of AAV genome are retained in the rAAV vector. A rAAV is distinguished from an AAV genome since all or a part of the AAV genome has been replaced with a non-native sequence with respect to the AAV genomic nucleic acid, such as with a heterologous nucleic acid encoding a therapeutic protein or polynucleotide sequence. Incorporation of a non-native sequence therefore defines the AAV as a "recombinant" AAV vector, which can be referred to as a "rAAV vector."

A recombinant AAV vector sequence can be packaged—referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV" or "rAAV particle" or "rAAV virion." Such rAAV, rAAV particles and rAAV virions include proteins that encapsidate or package the vector genome. Particular examples include in the case of AAV, capsid proteins.

A vector "genome" refers to the portion of the recombinant plasmid sequence that is ultimately packaged or encapsidated to form a rAAV particle. In cases where recombinant plasmids are used to construct or manufacture recombinant AAV vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into rAAV particles. Thus, a vector "genome" refers to the nucleic acid that is packaged or encapsidated by rAAV.

"AAV helper functions" refer to AAV-derived coding sequences (proteins) which can be expressed to provide AAV gene products and AAV vectors that, in turn, function in trans for productive AAV replication and packaging. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products (capsids) supply necessary packaging functions. AAV helper functions are used to complement AAV functions in trans that are missing from AAV vector genomes.

An "AAV helper construct" refers generally to a nucleic acid sequence that includes nucleotide sequences providing AAV functions deleted from an AAV vector which is to be used to produce a transducing AVV vector for delivery of a nucleic acid sequence of interest, by way of gene therapy to a subject, for example. AAV helper constructs are commonly used to provide transient expression of AAV rep and/or cap genes to complement missing AAV functions that are necessary for AAV vector replication. Helper constructs generally lack AAV ITRs and can neither replicate nor package themselves. AAV helper constructs can be in the form of a plasmid, phage, transposon, cosmid, virus, or virion. A number of AAV helper constructs have been described, such as plasmids pAAV/Ad and pIM29+45 which encode both Rep and Cap expression products (See, e.g., Samulski et al. (1989) J. Virol. 63:3822-3828; and McCarty et al. (1991) J. Virol. 65:2936-2945). A number of other vectors have been described which encode Rep and/or Cap expression products (See, e.g., U.S. Pat. Nos. 5,139,941 and 6,376,237).

The term "accessory functions" refers to non-AAV derived viral and/or cellular functions upon which AAV is dependent for replication. The term includes proteins and RNAs that are required in AAV replication, including moieties involved in activation of AAV gene transcription, stage specific AAV mRNA splicing, AAV DNA replication, synthesis of Cap expression products and AAV capsid packaging. Viral-based accessory functions can be derived from any of the known helper viruses such as adenovirus, herpesvirus (other than herpes simplex virus type-1) and vaccinia virus.

An "accessory function vector" refers generally to a nucleic acid molecule that includes polynucleotide sequences providing accessory functions. Such sequences can be on an accessory function vector, and transfected into a suitable host cell. The accessory function vector is capable of supporting rAAV virion production in the host cell. Accessory function vectors can be in the form of a plasmid, phage, transposon or cosmid. In addition, the full-complement of adenovirus genes are not required for accessory functions. For example, adenovirus mutants incapable of DNA replication and late gene synthesis have been reported to be permissive for AAV replication (Ito et al., (1970) J. Gen. Virol. 9:243; Ishibashi et al, (1971) Virology 45:317). Similarly, mutants within E2B and E3 regions have been shown to support AAV replication, indicating that the E2B and E3 regions are probably not involved in providing accessory functions (Carter et al., (1983) Virology 126:505). Adenoviruses defective in the E1 region, or having a deleted E4 region, are unable to support AAV replication. Thus, E1A and E4 regions appear necessary for AAV replication, either directly or indirectly (Laughlin et al., (1982) J. Virol. 41:868; Janik et al., (1981) Proc. Natl. Acad. Sci. USA 78:1925; Carter et al., (1983) Virology 126:505). Other characterized Adenovirus mutants include: E1B (Laughlin et al. (1982), supra; Janik et al. (1981), supra; Ostrove et al., (1980) Virology 104:502); E2A (Handa et al., (1975) J. Gen.

Virol. 29:239; Strauss et al., (1976) J. Virol. 17:140; Myers et al., (1980) J. Virol. 35:665; Jay et al., (1981) Proc. Natl. Acad. Sci. USA 78:2927; Myers et al., (1981) J. Biol. Chem. 256:567); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)). Studies of the accessory functions provided by adenoviruses having mutations in the E1B coding region have produced conflicting results, but E1B55k may be required for AAV virion production, while E1B19k is not (Samulski et al., (1988) J. Virol. 62:206-210). In addition, International Publication WO 97/17458 and Matshushita et al., (1998) Gene Therapy 5:938-945, describe accessory function vectors encoding various Adenovirus genes. Exemplary accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such accessory function vectors are described, for example, in International Publication No. WO 01/83797.

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Cross-reactivity differences are usually due to differences in capsid protein sequences/antigenic determinants (e.g., due to VP1, VP2, and/or VP3 sequence differences of AAV serotypes).

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

rAAV vectors include any viral strain or serotype. As a non-limiting example, a rAAV plasmid or vector genome or particle (capsid) can be based upon any AAV serotype, such as AAV-1, -2, -3, -4, -5, -6, -7, -8, -9, -10, -11, for example. Such vectors can be based on the same of strain or serotype (or subgroup or variant), or be different from each other. As a non-limiting example, a rAAV plasmid or vector genome or particle (capsid) based upon one serotype genome can be identical to one or more of the capsid proteins that package the vector. In addition, a rAAV plasmid or vector genome can be based upon an AAV (e.g., AAV2) serotype genome distinct from one or more of the capsid proteins that package the vector genome, in which case at least one of the three capsid proteins could be a AAV1, AAV2, AAV3, AAV4, AAV5, AAV6, AAV7, AAV8, AAV9, AAV10, AAV11, or variant thereof, for example. rAAV vectors therefore include gene/protein sequences identical to gene/protein sequences characteristic for a particular serotype, as well as mixed serotypes.

In various exemplary embodiments, a rAAV vector includes or consists of a capsid sequence at least 70% or more (e.g., 75%, 80%, 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, or AAV11 capsid proteins. In various exemplary embodiments, a rAAV vector includes or consists of a sequence at least 70% or more (e.g., 75%, 80%, 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, or AAV11 ITR(s).

rAAV, such as AAV1, AAV2, AAV3, AAV4, AAV5, AAV6, AAV7, AAV8, AAV9, AAV10, and AAV11, and variant, hybrid and chimeric sequences, can be constructed using recombinant techniques that are known to the skilled artisan, to include one or more heterologous polynucleotide sequences (transgenes) flanked with one or more functional AAV ITR sequences. Such vectors have one or more of the wild type AAV genes deleted in whole or in part, but retain at least one functional flanking ITR sequence(s), as necessary for the rescue, replication, and packaging of the recombinant vector into a rAAV vector particle. A rAAV vector genome would therefore include sequences required in cis for replication and packaging (e.g., functional ITR sequences)

The terms "nucleic acid" and "polynucleotide" are used interchangeably herein to refer to all forms of nucleic acid, oligonucleotides, including deoxyribonucleic acid (DNA) and ribonucleic acid (RNA). Nucleic acids include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Nucleic acids include naturally occurring, synthetic, and intentionally modified or altered polynucleotides. Nucleic acids can be single, double, or triplex, linear or circular, and can be of any length. In discussing nucleic acids, a sequence or structure of a particular polynucleotide may be described herein according to the convention of providing the sequence in the 5' to 3' direction.

A "heterologous" nucleic acid sequence refers to a polynucleotide inserted into a AAV plasmid or vector for purposes of vector mediated transfer/delivery of the polynucleotide into a cell. Heterologous nucleic acid sequences are distinct from AAV nucleic acid, i.e., are non-native with respect to AAV nucleic acid. Once transferred/delivered into the cell, a heterologous nucleic acid sequence, contained within the vector, can be expressed (e.g., transcribed, and translated if appropriate). Alternatively, a transferred/delivered heterologous polynucleotide in a cell, contained within the vector, need not be expressed. Although the term "heterologous" is not always used herein in reference to nucleic acid sequences and polynucleotides, reference to a nucleic acid sequence or polynucleotide even in the absence of the modifier "heterologous" is intended to include heterologous nucleic acid sequences and polynucleotides in spite of the omission.

The "polypeptides," "proteins" and "peptides" encoded by the "nucleic acid sequence," include full-length native sequences, as with naturally occurring proteins, as well as functional subsequences, modified forms or sequence variants so long as the subsequence, modified form or variant retains some degree of functionality of the native full-length protein. Such polypeptides, proteins and peptides encoded by the nucleic acid sequences can be but are not required to be identical to the endogenous protein that is defective, or whose expression is insufficient, or deficient in the treated mammal.

A "transgene" is used herein to conveniently refer to a nucleic acid (e.g., heterologous) that is intended or has been introduced into a cell or organism. Transgenes include any nucleic acid, such as a heterologous nucleic acid encoding a therapeutic protein or polynucleotide sequence.

In a cell having a transgene, the transgene has been introduced/transferred by way of a plasmid or a AAV vector, "transduction" or "transfection" of the cell. The terms "transduce" and "transfect" refer to introduction of a molecule such as a nucleic acid into a host cell (e.g., HEK293) or cells of an organism. The transgene may or may not be integrated into genomic nucleic acid of the recipient cell. If an introduced nucleic acid becomes integrated into the nucleic acid (genomic DNA) of the recipient cell or organism it can be stably maintained in that cell or organism and further passed on to or inherited by progeny cells or organisms of the recipient cell or cells of an organism.

A "host cell" denotes, for example, microorganisms, yeast cells, insect cells, and mammalian cells, that can be, or have been, used as recipients of an AAV vector plasmid, AAV helper construct, an accessory function vector, or other transfer DNA. The term includes the progeny of the original cell which has been transfected. Thus, a "host cell" generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. Exemplary host cells include human embryonic kidney (HEK) cells such as HEK293.

A "transduced cell" is a cell into which a transgene has been introduced. Accordingly, a "transduced" cell means a genetic change in a cell following incorporation of an exogenous molecule, for example, a nucleic acid (e.g., a transgene) into the cell. Thus, a "transduced" cell is a cell into which, or a progeny thereof in which an exogenous nucleic acid has been introduced. The cell(s) can be propagated (cultured) and the introduced protein expressed or nucleic acid transcribed, or vector, such as rAAV, produced by the cell. For gene therapy uses and methods, a transduced cell can be in a subject.

As used herein, the term "stable" in reference to a cell, or "stably integrated" means that nucleic acid sequences, such as a selectable marker or heterologous nucleic acid sequence, or plasmid or vector has been inserted into a chromosome (e.g., by homologous recombination, non-homologous end joining, transfection, etc.) or is maintained in the recipient cell or host organism extrachromosomally, and has remained in the chromosome or is maintained extrachromosomally for a period of time. In the case of culture cells, nucleic acid sequences, such as a heterologous nucleic acid sequence, or plasmid or vector has been inserted into a chromosome can be maintained over the course of a plurality of cell passages.

A "cell line" refers to a population of cells capable of continuous or prolonged growth and division in vitro under appropriate culture conditions. Cell lines can, but need not be, clonal populations derived from a single progenitor cell. In cell lines, spontaneous or induced changes can occur in karyotype during storage or transfer of such clonal populations, as well as during prolonged passaging in tissue culture. Thus, progeny cells derived from the cell line may not be precisely identical to the ancestral cells or cultures. An exemplary cell line applicable to the invention purification methods is HEK293.

An "expression control element" refers to nucleic acid sequence(s) that influence expression of an operably linked nucleic acid. Control elements, including expression control elements as set forth herein such as promoters and enhancers. rAAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of rAAV vectors, expression control elements will typically be within 1 to 1000 nucleotides from the transcribed nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence. A promoter typically increases an amount expressed from operably linked nucleic acid as compared to an amount expressed when no promoter exists.

An "enhancer" as used herein can refer to a sequence that is located adjacent to the nucleic acid sequence, such as selectable marker, or heterologous nucleic acid sequence Enhancer elements are typically located upstream of a promoter element but also function and can be located downstream of or within a sequence. Hence, an enhancer element can be located upstream or downstream, e.g., within 100 base pairs, 200 base pairs, or 300 or more base pairs of the as selectable marker, and/or a heterologous nucleic acid encoding a therapeutic protein or polynucleotide sequence. Enhancer elements typically increase expression of an operably linked nucleic acid above expression afforded by a promoter element.

The term "operably linked" means that the regulatory sequences necessary for expression of a nucleic acid sequence are placed in the appropriate positions relative to the sequence so as to effect expression of the nucleic acid sequence. This same definition is sometimes applied to the arrangement of nucleic acid sequences and transcription control elements (e.g. promoters, enhancers, and termination elements) in an expression vector, e.g., rAAV vector.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for vector packaging into a rAAV particle. In various embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

A "therapeutic protein" in one embodiment is a peptide or protein that may alleviate or reduce symptoms that result from an insufficient amount, absence or defect in a protein in a cell or subject. A "therapeutic" protein encoded by a transgene can confer a benefit to a subject, e.g., to correct a genetic defect, to correct a gene (expression or functional) deficiency, etc.

Non-limiting examples of heterologous nucleic acids encoding gene products (e.g., therapeutic proteins) which are useful in accordance with the invention include those that may be used in the treatment of a disease or disorder including, but not limited to, "hemostasis" or blood clotting disorders such as hemophilia A, hemophilia A patients with inhibitory antibodies, hemophilia B, deficiencies in coagulation Factors, VII, VIII, IX and X, XI, V, XII, II, von Willebrand factor, combined FV/FVIII deficiency, thalassemia, vitamin K epoxide reductase C1 deficiency, gamma-carboxylase deficiency; anemia, bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

Nucleic acid molecules, vectors such as cloning, expression vectors (e.g., vector genomes) and plasmids, may be prepared using recombinant DNA technology methods. The availability of nucleotide sequence information enables preparation of nucleic acid molecules by a variety of means. For example, a heterologous nucleic acid encoding Factor IX (FIX) comprising a vector or plasmid can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane.

With respect to protein, the term "isolated protein" or "isolated and purified protein" is sometimes used herein. This term refers primarily to a protein produced by expression of a nucleic acid molecule. Alternatively, this term may refer to a protein which has been sufficiently separated from other proteins with which it would naturally be associated, so as to exist in "substantially pure" form.

The term "isolated" does not exclude combinations produced by the hand of man, for example, a recombinant rAAV and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or about 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given sequence. For example, when used in reference to an amino acid sequence, the phrase includes the sequence per se and molecular modifications that would not affect the basic and novel characteristics of the sequence.

Methods that are known in the art for generating rAAV virions: for example, transfection using AAV vector and AAV helper sequences in conjunction with coinfection with one AAV helper viruses (e.g., adenovirus, herpesvirus, or vaccinia virus) or transfection with a recombinant AAV vector, an AAV helper vector, and an accessory function vector. Non-limiting methods for generating rAAV virions are described, for example, in U.S. Pat. Nos. 6,001,650 and 6,004,797. Following recombinant rAAV vector production (i.e. vector generation in cell culture systems), rAAV virions can be obtained from the host cells and cell culture supernatant and purified as set forth herein.

As an initial step, typically host cells that produce the rAAV virions can be harvested, optionally in combination with harvesting cell culture supernatant in which the host cells producing rAAV virions have been cultured. In methods herein, the harvested cells and optionally cell culture supernatant may be used as is, as appropriate, or concentrated. Further, if infection is employed to express accessory functions, residual helper virus can be inactivated. For example, adenovirus can be inactivated by heating to temperatures of approximately 60° C. for, e.g., 20 minutes or more, which inactivates only the helper virus since AAV is heat stable while the helper adenovirus is heat labile.

Supernatant and cells of the harvest are lysed by disrupting the cells, for example, by microfuidization, to release the rAAV particles. Subsequently, a nuclease such as benzonase may be added to degrade contaminating DNA. Typically, the resulting lysate is clarified to remove cell debris, such as filtering, centrifuging, to render a clarified cell lysate. In a particular example, lysate is filtered with a micron diameter pore size filter (for example, through a 0.45 am and/or 0.2 am filter), to produce a clarified lysate.

The clarified lysate contains AAV particles (bona fide rAAV vectors, and AAV empty capsids) and AAV vector production related impurities, such as soluble cellular components from the host cells that can include cellular proteins, lipids, and/or nucleic acids, and cell culture medium components. Clarified lysate is then subjected to additional purification steps to purify AAV particles (including bona fide rAAV vectors) from impurities using chromatography. Clarified lysate may be diluted with an appropriate buffer prior to the first step of chromatography.

A plurality of sequential chromatography steps are typically used to purify rAAV particles. Such methods typically exclude a step of cesium chloride gradient ultracentrifugation.

As disclosed herein, a first chromatography step may be anion exchange chromatography or cation exchange chromatography. If the first chromatography step is anion exchange chromatography the third chromatography step can be cation exchange chromatography. Thus, in one rAAV purification method, purification is via anion exchange chromatography, followed by purification via size exclusion chromatography followed by purification via cation exchange chromatography.

If the first chromatography step is cation exchange chromatography than the third chromatography step can be anion exchange chromatography. Thus, in another rAAV purification method, purification is via cation exchange chromatography, followed by purification via size exclusion chromatography, followed by purification via anion exchange chromatography.

Anion exchange chromatography functions to separate AAV particles from proteins, cellular and other components present in the clarified lysate and/or column eluate from the size exclusion chromatography. Anion exchange resins include, without limitation, those based on polyamine resins and other resins. Examples of strong anion exchange resins include those based generally on the quaternized nitrogen atom including, without limitation, quaternary ammonium salt resins such as trialkylbenzyl ammonium resins. Suitable exchange chromatography include without limitation, MACRO PREP Q (strong anion-exchanger available from BioRad, Hercules, Calif.); UNOSPHERE Q (strong anion-exchanger available from BioRad, Hercules, Calif.); POROS 50HQ (strong anion-exchanger available from Applied Biosystems, Foster City, Calif.); POROS 50D (weak anion-exchanger available from Applied Biosystems, Foster City, Calif.); POROS 50PI (weak anion-exchanger available from Applied Biosystems, Foster City, Calif.); SOURCE 30Q (strong anion-exchanger available from Amersham Biosciences, Piscataway, N.J.); DEAE SEPHAROSE (weak anion-exchanger available from Amersham Biosciences, Piscataway, N.J.); Q SEPHAROSE (strong anion-exchanger available from Amersham Biosciences, Piscataway, N.J.). Additional exemplary anion exchange resins include aminoethyl (AE), diethylaminoethyl (DEAE), diethylaminopropyl (DEPE) and quaternary amino ethyl (QAE).

Cation exchange chromatography functions to further separate the AAV particles from cellular and other components present in the clarified lysate and/or column eluate from the size exclusion chromatography. Examples of strong cation exchange resins capable of binding rAAV virions over a wide pH range include, without limitation, any sulfonic acid based resins as indicated by the presence of the sulfonate functional group, including aryl and alkyl substituted sulfonates, such as sulfopropyl or sulfoethyl resins. Representative matrices include but are not limited to POROS HS, POROS HS 50, POROS SP, POROS S (strong cation exchangers available from Applied Biosystems, Foster City, Calif.). Additional examples include commercial DOWEX®, AMBERLITE®, and AMBERLYST® families of resins available from Aldrich Chemical Company (Milliwaukee, Wis.). Weak cation exchange resins include, without limitation any carboxylic acid based resins. Exemplary cation exchange resins include carboxymethyl (CM), phospho (based on the phosphate functional group), methyl sulfonate (S) and sulfopropyl (SP) resins.

Chromatography medium such as cation exchange, anion exchange and size exclusion can be equilibrated, washed and eluted with various buffers under various conditions such as pH, and buffer volumes. The following is intended to describe particular non-limiting examples, but is not intended to limit the invention.

Cation exchange chromatography may be equilibrated using standard buffers and according to the manufacturer's specifications. For example, chromatography media can be equilibrated with an acetate buffer, at 5 to 50 mM, or 10-40 mM, such as 10-30 mM, and sodium chloride. After equilibration, sample is then loaded. Subsequently, the chromatography media is washed at least once, or more, e.g., 2-5 times. Elution from the chromatography media is by way of a high salt buffer, at least once, but elution may be 2 or more times with the same or a higher salt buffer.

Typical equilibration buffers and solutions for washes and elutions for cation exchange chromatography are at an appropriate pH, of from about pH 3 to pH 8, more typically from about pH 4 to pH 6, such as pH 4.1, 4.2, 4.3, 4.4. 4.5-5.5, 5.6, 5.7, 5.8, 5.9, or 6.0 or any pH at or between the stated ranges.

Appropriate equilibration buffers and solutions for washes and elutions for cation exchange columns are known in the art and are generally anionic. Such buffers include, without limitation, buffers with the following buffer ions: phosphate, acetate, citrate, borate, or sulfate.

In one embodiment, the cation exchange chromatography media is first equilibrated, sample applied, and washed with a low salt concentration, e.g., 10-100 mM of NaCl, such as 10, 20, 25, 30, 35, 40, 45, 50, 55, 60, 60-100 mM, or any concentration at or within these ranges. Following sample application, the chromatography media may be treated with a higher salt concentration in order to elute impurities, such as a higher NaCl concentration, or with another buffer with a greater ionic strength. One example for use as the second buffer is an acetate buffer with a NaCl concentration of 100 mM-200 mM, or any concentration at or within these stated ranges. After additional impurities are eluted from the column, to elute AAV particles, the ionic strength of the buffer may be increased using a salt, such as NaCl, KCl, sulfate, formate or acetate, and recovered.

In the anion exchange chromatography media wash solutions, polyethylene glycol (PEG) may be included. This is referred to as polyethylene glycol (PEG) modulated column chromatography. PEG wash solutions can be applied to the anion exchange chromatography media prior to elution of AAV vector particles.

Typical equilibration buffers and solutions for washes and elutions for anion exchange chromatography an appropriate at a pH of from about pH 5 to pH 12, more typically from about pH 6 to pH 10, and even more typically from about pH 7 to pH 9.5, such as pH 7.1, 7.2, 7.3, 7.4-8.0, 8.1, 8.2, 8.3, 8.4, 8.5-9.0, 9.1, 9.2, 9.3, 9.4, 9.5, or any pH at or between the stated ranges.

Appropriate equilibration buffers and solutions for washes and elutions for anion exchange columns are known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate.

In one embodiment, the anion exchange chromatography media is first equilibrated, sample applied, and washed with a low salt concentration, e.g., 10-100 mM of NaCl, such as 10, 20, 25, 30, 35, 40, 45, 50, 55, 60, 60-100 mM, or any concentration at or within these ranges. Following sample application, the chromatography media may be treated with a higher salt concentration in order to elute impurities, such as a higher NaCl concentration, or with another buffer with a greater ionic strength. One example for use as the second buffer is a Tris-based buffer with a NaCl concentration of 100 mM-200 mM, or any concentration at or within these stated ranges. After additional impurities are eluted from the column, the AAV particles can be recovered using a higher concentration of salt.

In the anion exchange chromatography media wash solutions, polyethylene glycol (PEG) may be included. This is referred to as polyethylene glycol (PEG) modulated column chromatography. PEG wash solutions can be applied to the anion exchange chromatography media prior to elution of AAV vector particles.

Typically PEG in such wash solutions have an average molecular weight in a range of about 1,000 to 50,000, inclusive. Typical amounts of PEG in such wash solutions range from about 0.1% to about 20% PEG or any amount at or within these stated ranges, or from about 1% to about 10% PEG or any amount at or within these stated ranges.

Size-exclusion chromatography media may be equilibrated using standard buffers and according to the manufacturer's specifications. For example, chromatography media can be equilibrated with a phosphate buffer, for example, at 1 to 5 mM, 5 to 50 mM, or 5-25 mM, and sodium chloride, for example, at 25 to 50 mM, 50 to 100 mM, 100-150 mM or 125-175 mM.

After equilibration, sample is then loaded. Subsequently, the flow through containing the AAV particles is recovered. Additional volumes of buffer (e.g., phosphate buffer), based upon the amount of chromatography media and/or column size, can be added for AAV particle recovery.

In particular embodiments, size exclusion chromatography media has a separation range (Molecular weight) between about 10,000 and 600,000, inclusive. Particular resins (media) appropriate for size exclusion chromatography include without limitation particles or beads of porous cellulose, crosslinked agarose (Sepharose), crosslinked dextran (Sephadex), styrene-divinylbenzene (Dianon HP-20), polyacrylamide (Bio Gel), methacrylic (Toyopearl), and controlled pore glass.

Volumes of buffer for elution can be based upon the amount of chromatography media and/or column size to achieve AAV particle recovery. Typical volumes are 1-10 column volumes.

Column eluate is/are collected following the elution(s)/flow through from each of the chromatography steps. AAV can be detected in the fractions using standard techniques, such as monitoring UV absorption at 260 and 280 nm.

The use of cation or anion exchange chromatography media, the nature of the media used (i.e. strong or weak ion exchangers) and conditions of salt concentration, buffer used, and pH, can vary based upon the AAV capsid (i.e. AAV capsid serotype or pseudotype). While AAV capsid structure typically share features such as size and shape, capsids may have different amino acid sequences that result in subtle differences of molecular topology and surface charge distribution. Thus, capsid sequence variants are expected to be amenable to purification by the methods of the invention, and relevant methods can be determined in a systematic manner using chromatography media and buffer screening studies, to determine if different conditions will be used for a AAV capsid variant for AAV particle purification.

Eluates comprising AAV particles from any of the anion, size exclusion, or cation exchange chromatography steps as described herein can, if desired, be efficiently concentrated by ultrafiltration/diafiltration. Reduction in volume can be controlled by the skilled artisan. In particular non-limiting examples the reduction in volume achieved is between abut 1-20 fold, inclusive. Thus, a 1-fold reduction reduces the volume by half, e.g., 1000 ml is concentrated to 500 mL. A 10 fold reduction reduces the volume by a factor of 10, e.g., 2000 ml is concentrated to 200 mL. A 20 fold reduction reduces the volume by a factor of 20, e.g., 2000 ml is concentrated to 100 mL.

A non-limiting example of ultrafiltration/diafiltration is tangential flow filtration (TFF). For example a hollow fiber membrane with a nominal pore size corresponding to a 100 kDa molecular weight cutoff, so that large amounts of AAV vector can be prepared when present in larger volumes of eluate.

Methods of the invention achieve substantial recovery of AAV particles. For example, methods of the invention achieve recovery of AAV particles of approximately 40-70% of the total rAAV vector particles from the host cells and host cell culture supernatant harvested. In another example, AAV particles are present in the final (e.g., third column) eluate at a concentration of about 100 mg/mL. AAV vector particles may be present in the final (e.g., third column) eluate at a concentration of $10^{15}$ particles per mL, or more, $10^{16}$ particles per mL, $10^{17}$ particles per mL.

Alternatively, if AAV vector particle concentrations are less, purified AAV particles can be concentrated. For example, purified AAV particles can be concentrated to $10^{15}$ particles per mL by ultrafiltration/diafiltration (e.g., TFF). If higher concentrations of vector are desired, purified AAV particles can be concentrated to $10^{16}$ particles per mL by ultrafiltration/diafiltration (e.g., TFF), or even higher.

The combination of purification of AAV particles from clarified cell lysates by an all column chromatography process, and concentration (if necessary) of purified AAV particles by ultrafiltration/diafiltration (e.g., TFF), provides large quantities of highly purified recombinant rAAV vector.

In other embodiments, rAAV virions with packaged genomes (i.e., bona fide rAAV vector particles) are "substantially free of "AAV-encapsidated nucleic acid impurities" when at least about 60% or more of the virions present are rAAV virions with packaged genomes (i.e., bona fide rAAV vector particles). Production of rAAV virions with packaged genomes (i.e., bona fide rAAV vector particles) substantially free of AAV-encapsidated nucleic acid impurities can be from about 40% to about 20% or less, about 20% to about 10%, or less, about 10% to about 5% or less, about 5% to about 1% or less than 1% or less of the product comprises AAV-encapsidated nucleic acid impurities.

Methods to determine infectious titer of AAV vector containing a transgene are known in the art (See, e.g., Zhen et al., (2004) Hum. Gene Ther. (2004) 15:709). Methods for assaying for empty capsids and AAV vector particles with packaged genomes are known (See, e.g., Grimm et al., Gene Therapy (1999) 6:1322-1330; Sommer et al., Molec. Ther. (2003) 7:122-128).

To determine degraded/denatured capsid, purified AAV can be subjected to SDS-polyacrylamide gel electrophoresis, consisting of any gel capable of separating the three capsid proteins, for example, a gradient gel, then running the gel until sample is separated, and blotting the gel onto nylon or nitrocellulose membranes. Anti-AAV capsid antibodies are then used as primary antibodies that bind to denatured capsid proteins (See, e.g., Wobus et al., J. Virol. (2000) 74:9281-9293). A secondary antibody that binds to the primary antibody contains a means for detecting the primary antibody. Binding between the primary and secondary antibodies is detected semi-quantitatively to determine the amount of capsids.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., nucleic acid sequences, vectors, rAAV vectors, etc.) are an example of a genus of equivalent or similar features.

As used herein, the singular forms "a", "and," and "the" include plural referents unless the context clearly indicates otherwise. Thus, for example, reference to "an AAV vector," or "AAV particle," includes a plurality of such AAV vectors and AAV particles, and reference to "a cell" or "host cell" includes a plurality of cells and host cells.

The term "about" as used herein means values that are within 10% (plus or minus) of a reference value.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges are inclusive. Further, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

What is claimed is:

1. A method for purifying recombinant adeno-associated (rAAV) vector particles said method comprising the steps of:
   (a) harvesting cells and cell culture supernatant comprising rAAV vector particles to produce a harvest;
   (b) optionally concentrating said harvest produced in step (a) to produce a concentrated harvest;
   (c) lysing said harvest produced in step (a) or said concentrated harvest produced in step (b) to produce a lysate;
   (d) treating the lysate produced in step (c) to reduce contaminating nucleic acid in the lysate thereby producing a nucleic acid reduced lysate;
   (e) filtering said nucleic acid reduced lysate produced in step (d) to produce a clarified lysate, and optionally diluting said clarified lysate to produce a diluted clarified lysate;
   (f) subjecting said clarified lysate or diluted clarified lysate produced in step (e) to anion exchange column chromatography to produce a column eluate comprised of rAAV vector particles, and optionally concentrating said column eluate to produce a concentrated column eluate;
   (g) subjecting said column eluate or said concentrated column eluate produced in step (f) to size exclusion column chromatography to produce a second column eluate comprised of rAAV vector particles thereby separating rAAV vector particles from protein impurities, and optionally diluting said second column eluate to produce a diluted second column eluate;
- (h) subjecting said second column eluate or said diluted second column eluate produced in step (g) to cation exchange column chromatography to produce a third column eluate comprised of rAAV vector particles thereby separating rAAV vector particles from protein or other production impurities, and optionally concentrating said third column eluate to produce a concentrated third column eluate; and
- (i) filtering said third column eluate or said concentrated third column eluate produced in step (h) thereby producing purified rAAV vector particles.

2. A method according to claim 1, wherein said concentrating of step (b) and/or step (f) and/or step (h) is via is by ultrafiltration/diafiltration, optionally by tangential flow filtration.

3. A method according to claim 1, wherein said lysing of said harvest produced in step (a) or said concentrated harvest produced in step (b) is by microfluidization.

4. A method according to claim 1, wherein step (d) comprises treating with a nuclease thereby reducing contaminating nucleic acid.

5. A method according to claim 1, wherein said filtering said clarified lysate or said diluted clarified lysate of step (e) is via a filter having a pore diameter of between about 0.1 and 0.8 microns, inclusive.

6. A method according to claim 1, wherein said diluting said clarified lysate or said diluted clarified lysate of step (e) is with an aqueous buffered acetate solution.

7. A method according to claim 1, wherein said diluting of said second column eluate of step (g) is with an aqueous buffered acetate solution.

8. A method according to claim 1, wherein said rAAV vector particles resulting from step (i) are formulated with a surfactant to produce an AAV vector formulation.

9. A method according to claim 1, wherein said anion exchange column chromatography of step (f) comprises polyethylene glycol (PEG) modulated column chromatography.

10. A method according to claim 1, wherein said anion exchange column of step (f) comprises washing said column with an aqueous surfactant solution prior to elution of said rAAV vector particles from the column.

11. A method according to claim 1, wherein said cation exchange column of step (h) comprises washing said column with a surfactant solution prior to elution of said rAAV vector particles from the column.

12. A method according to claim 1, wherein said rAAV vector particles are eluted from said anion exchange column of step (f) in an aqueous Tris-Cl/NaCl buffer.

13. A method according to claim 1, wherein said rAAV vector particles are eluted from said cation exchange column of step (h) in an aqueous phosphate/NaCl buffer.

14. A method according to claim 1, wherein the method excludes a step of cesium chloride gradient ultracentrifugation.

15. A method according to claim 1, wherein said rAAV vector particles comprise a transgene that is transcribed into a nucleic acid selected from the group consisting of a siRNA, an antisense molecule, miRNA a ribozyme and a shRNA.

16. A method according to claim 1, wherein said rAAV vector particles comprise a transgene that encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

17. A method according to claim 1, wherein said rAAV vector particles comprise a transgene that encodes a gene product selected from the group consisting of thrombopoietin (TPO), interleukins (IL1 through IL-17), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, class I and class II MHC molecules.

18. A method according to claim 1, wherein said rAAV vector particles comprise a transgene encoding a protein useful for correction of in born errors of metabolism selected from the group consisting of carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, RPE65, H-protein, T-protein, a cystic fibrosis transmembrane regulator (CFTR) sequence, and a dystrophin cDNA sequence.

19. A method according to claim 1, wherein the method recovers approximately 40-70% of the total rAAV vector particles from the harvest produced in step (a) or said concentrated harvest produced in step (b).

20. A method according to claim 1, wherein the method produces rAAV vector particles having a greater purity than rAAV vector particles produced or purified by AAV affinity column purification.

21. A method according to claim 1, wherein the method produces rAAV vector particles having a greater purity than rAAV vector particles produced or purified by an AAV affinity column combined with an anion exchange column purification.

22. A method according to claim 1, wherein the method produces rAAV vector particles having a greater purity than rAAV vector particles produced or purified by an AAV affinity column combined with an anion exchange column and a cation exchange purification.

23. A method according to claim 1, wherein said rAAV vector particles are derived from an AAV selected from the group consisting of AAV1, AAV2, AAV3, AAV4, AAV5, AAV6, AAV7, AAV8, AAV9 and AAV10.

24. A method for purifying recombinant adeno-associated (rAAV) vector particles said method comprising the steps of:
(a) harvesting cells and cell culture supernatant comprising rAAV vector particles to produce a harvest;
(b) optionally concentrating said harvest produced in step (a) to produce a concentrated harvest;
(c) lysing said harvest produced in step (a) or said concentrated harvest produced in step (b) to produce a lysate;
(d) treating the lysate produced in step (c) to reduce contaminating nucleic acid in the lysate thereby producing a nucleic acid reduced lysate;
(e) filtering said nucleic acid reduced lysate produced in step (d) to produce a clarified lysate, and optionally diluting said clarified lysate to produce a diluted clarified lysate;
(f) subjecting said clarified lysate or diluted clarified lysate produced in step (e) to cation exchange column chromatography to produce a column eluate comprised of rAAV vector particles thereby separating rAAV vector particles from protein or other production impurities, and optionally concentrating said column eluate to produce a concentrated column eluate;
(g) subjecting said column eluate or said concentrated column eluate produced in step (f) to size exclusion column chromatography to produce a second column eluate comprised of rAAV vector particles thereby separating rAAV vector particles from protein impurities, and optionally diluting said second column eluate to produce a diluted second column eluate;
(h) subjecting said second column eluate or said diluted second column eluate produced in step (g) to anion exchange column chromatography to produce a third column eluate comprised of rAAV vector particles, and optionally concentrating said third column eluate to produce a concentrated third column eluate; and
(i) filtering said third column eluate or said concentrated third column eluate produced in step (h) thereby producing purified rAAV vector particles.

25. A method according to claim 24, wherein said concentrating of step (b) and/or step (f) and/or step (h) is via is by ultrafiltration/diafiltration, optionally by tangential flow filtration.

26. A method according to claim 24, wherein said lysing of said harvest produced in step (a) or said concentrated harvest produced in step (b) is by microfluidization.

27. A method according to claim 24, wherein step (d) comprises treating with a nuclease thereby reducing contaminating nucleic acid.

28. A method according to claim 24, wherein said filtering said clarified lysate or said diluted clarified lysate of step (e) is via a filter having a pore diameter of between about 0.1 and 0.8 microns, inclusive.

29. A method according to claim 24, wherein said diluting said clarified lysate or said diluted clarified lysate of step (e) is with an aqueous buffered acetate solution.

30. A method according to claim 24, wherein said diluting of said second column eluate of step (g) is with an aqueous buffered acetate solution.

31. A method according to claim 24, wherein said rAAV vector particles resulting from step (i) are formulated with a surfactant to produce an AAV vector formulation.

32. A method according to claim 24, wherein said anion exchange column chromatography of step (h) comprises polyethylene glycol (PEG) modulated column chromatography.

33. A method according to claim 24, wherein said anion exchange column chromatography of step (h) comprises washing said column with a PEG solution prior to elution of said rAAV vector particles from the column.

34. A method according to claim 24, wherein said anion exchange column of step (h) comprises washing said column with an aqueous surfactant solution prior to elution of said rAAV vector particles from the column.

35. A method according to claim 24, wherein said cation exchange column of step (f) comprises washing said column with a surfactant solution prior to elution of said rAAV vector particles from the column.

36. A method according to claim 24, wherein said rAAV vector particles are eluted from said anion exchange column of step (h) in an aqueous Tris-Cl/NaCl buffer.

37. A method according to claim 24, wherein said rAAV vector particles are eluted from said cation exchange column of step (f) in an aqueous phosphate/NaCl buffer.

38. A method according to claim 24, wherein the method excludes a step of cesium chloride gradient ultracentrifugation.

39. A method according to claim 24, wherein said rAAV vector particles comprise a transgene that is transcribed into a nucleic acid selected from the group consisting of a siRNA, an antisense molecule, miRNA a ribozyme and a shRNA.

40. A method according to claim 24, wherein said rAAV vector particles comprise a transgene that encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

41. A method according to claim 24, wherein said rAAV vector particles comprise a transgene that encodes a gene product selected from the group consisting of thrombopoietin (TPO), interleukins (IL1 through IL-17), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, class I and class II MHC molecules.

42. A method according to claim 24, wherein said rAAV vector particles comprise a transgene encoding a protein useful for correction of in born errors of metabolism selected from the group consisting of carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6- phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, RPE65, H-protein, T-protein, a cystic fibrosis transmembrane regulator (CFTR) sequence, and a dystrophin cDNA sequence.

43. A method according to claim 24, wherein the method recovers approximately 40-70% of the total rAAV vector particles from the harvest produced in step (a) or said concentrated harvest produced in step (b).

44. A method according to claim 24, wherein the method produces rAAV vector particles having a greater purity than rAAV vector particles produced or purified by AAV affinity column purification.

45. A method according to claim 24, wherein the method produces rAAV vector particles having a greater purity than rAAV vector particles produced or purified by an AAV affinity column combined with an anion exchange column purification.

46. A method according to claim 24, wherein the method produces rAAV vector particles having a greater purity than rAAV vector particles produced or purified by an AAV affinity column combined with an anion exchange column and a cation exchange purification.

47. A method according to claim 24, wherein said rAAV vector particles are derived from an AAV selected from the group consisting of AAV1, AAV2, AAV3, AAV4, AAV5, AAV6, AAV7, AAV8, AAV9 and AAV10.

* * * * *